(12) United States Patent
Park et al.

(10) Patent No.: US 6,979,431 B2
(45) Date of Patent: *Dec. 27, 2005

(54) METHOD FOR LABELLING TECHNETIUM OR RHENIUM USING BOROHYDRIDE EXCHANGE RESIN

(75) Inventors: Kyung Bae Park, Daejeon (KR); Sang Hyun Park, Seongnam-si (KR); Hui Jeong Gwon, Daejeon (KR); Sun Ju Choi, Daejeon (KR); Byung Chul Shin, Daejeon (KR); Young Don Hong, Daejeon (KR); Sang Mu Choi, Daejeon (KR); Woong Woo Park, Seoul (KR); Kwang Hee Han, Daejeon (KR); Beom Su Jang, Daejeon (KR)

(73) Assignee: Korea Atomic Energy Research Institute, Daejeon (KR)

( * ) Notice: Subject to any disclaimer, the term of this patent is extended or adjusted under 35 U.S.C. 154(b) by 454 days.

This patent is subject to a terminal disclaimer.

(21) Appl. No.: 10/253,515

(22) Filed: Sep. 24, 2002

(65) Prior Publication Data

US 2003/0194365 A1  Oct. 16, 2003

(30) Foreign Application Priority Data

Apr. 15, 2002 (KR) ............................... 2002-20298

(51) Int. Cl.⁷ ..................... C01B 17/20; A61K 51/00; C01G 47/00; C01G 57/00
(52) U.S. Cl. ................. 423/249; 423/561.1; 424/1.11; 424/1.65
(58) Field of Search ............ 423/49, 249, 561.1, 423/562; 424/1.11, 1.37, 1.49, 1.65, 1.69, 424/1.73; 534/7, 10–14; 206/223, 569, 570

(56) References Cited

U.S. PATENT DOCUMENTS 3,873,680 A  *  3/1975  Jackson et al. ............ 424/1.65
3,928,552 A  *  12/1975  Winchell et al. ........... 424/1.65
4,208,398 A  *  6/1980  Kubiatowicz et al. ...... 424/1.65
5,662,882 A  *  9/1997  Brodack et al. ............ 424/1.11
6,099,822 A  *  8/2000  Ozker et al. ................ 424/1.73
6,344,178 B1 *  2/2002  Alberto et al. ............. 424/1.65
2003/0120046 A1 *  6/2003  Lee et al. .................... 534/11
2003/0228255 A1 *  12/2003  Park et al. .................. 424/1.49

FOREIGN PATENT DOCUMENTS

WO   WO 98/488848   * 11/1998
WO   WO 01/70724    *  9/2001

OTHER PUBLICATIONS

An article entitled "Neutral and Stereospecific Tc-99m Complexes: . . . ," By Zhuang et al., published by Nuclear Medicine & Biology, vol. 26, pp. 217-224, 1999.
An article entitled "Small and Neutral TcvO BAT Bisaminoethanethiol (N2S2) . . . ," By Oya et al., published by Nuclear Medicine & Biology, vol. 25, pp. 135-140, 1998.
An article entitled "Preparation of 99mTc-N2S2 Conjugates of . . . ," By Dezutter et al., published by Journal of Labelled Compounds and Radiopharmaceuticals, vol. 42, pp. 309-324, 1999.

* cited by examiner

Primary Examiner—Stanley S. Silverman
Assistant Examiner—Ardith E. Hertzog
(74) Attorney, Agent, or Firm—Bachman & LaPointe, P.C.

(57) ABSTRACT

A method for labelling a sulfide compound with technetium or rhenium, comprising the reaction of a disulfide compound with pertechnetate or perrhenate in the presence of borohydride exchange resin to obtain a complex of technetium or rhenium with the sulfide compound. The method can directly label disulfide compounds with technetium or rhenium, can skip the synthetic step of thiol-protected S-precursor, and is useful for high value-added radiopharmaceuticals.

9 Claims, 10 Drawing Sheets

METHOD FOR LABELLING TECHNETIUM OR RHENIUM USING BOROHYDRIDE EXCHANGE RESIN

FIELD OF THE INVENTION

The present invention relates to a method for labelling disulfides with technetium or rhenium using a borohydride exchange resin. The present invention also relates to a kit for labelling technetium or rhenium.

BACKGROUND OF THE INVENTION

Technetium-99m ($^{99m}Tc$) is the most widely available radioisotope used for diagnostic radiophamarceuticals, with advantages of preferable properties for clinical use such as short half-life (6 h), gamma energy (140 keV) appropriate for obtaining gamma picture, low cost and general usefulness. $^{99m}Tc$ generally forms a complex with compounds having unpaired electrons such as isocyanate, amine, carboxyl, and thiol, and thus the complex formed is used as an imaging agent or a labelling agent of various tissues, which include lung, liver, and brain.

However, the method for the preparation of the technetium-radiolabelled thiol compound (hereinafter called a sulfide compound) is very limited because the compound containing thiol is very unstable. Accordingly, the compound is easily oxidized during the labelling reaction with $^{99m}Tc$, and forms a sulfide form and thus easily changes into a disulfide form [Cappozi, G. et al. The Chemistry of the Thiol Group, pt. 2; Wiley: N.Y., 1974, p. 785].

Up to now, the method for radiolabelling sulfide compound was carried out simultaneously with the chelation of technetium and the deprotection of the S-protected precursor synthesized in advance. For example, the method of labelling technetium for radiophamarceuticals is described in more detail in the following. First, a S-protected precursor is synthesized by being stirred with triphenylmethanol at room temperature under acidic catalysis for more than 1 hour; then the S-protected precursor is refluxed under acidic catalysis for more than 30 minutes before labelling $^{99m}Tc$; and finally $^{99m}Tc$ is labelled [Oya, s. et al. Nuclear Medicine and Biology 1998, 25, 135–140; Dezutter, A. *Journal of Labelled Compounds and phamarceuticals* 1999, 42, 309–324]. Using the above method, diamine dithiol as a ligand was synthesized, and the usefulness of the chelation for radiopharmaceuticals was recognized.

However, the above-mentioned method has disadvantages such as the S-protected precursor is synthesized through several steps and the deprotection of the S-protected precursor and the reduction of pertechnetate should be carried out simultaneously.

Among isotopes of rhenium, rhenium-186 ($^{186}Re$) and rhenium-188 ($^{188}Re$) are homologous elements with technetium, and they have the properties of emitting both beta ray that is appropriate for medical use and gamma ray that is possible picturing. Practically, $^{186}Re$ and $^{188}Re$ are being used as radiophamarceuticals that can be applied to the remedy of bone pain generated by secondary bone metastasis of prostate cancer, lung cancer, breast cancer, etc. Since $^{186}Re$ and $^{188}Re$ have similar chemical properties with technetium, the labelling method of technetium can be applied to the method of labelling rhenium through some improvements[Lin, W. et al. *J. Nucl. Med.* 1997, 24, 590–595; Lewington, V. J. et al. *Eur. J. Nucl. Med.* 1993, 20, 60–74; Lewington, V. J. et al. *Phys. Med. Biol.* 1996, 41, 2027–2042; Hashimoto, K. et al. *Appl. Radiat. Isot.* 1996, 47, 195–199].

Therefore, there have been continuous needs to develop a method which simultaneously carries out the reduction of disulfide compounds and reduction of pertechnetate or perrhenate under the mild condition, namely, a method to directly produce the technetium or rhenium complex with sulfide compounds from disulfide compounds is carried out.

Accordingly, the present inventors have completed the present invention in the course to develop a new labelling method that satisfies all the above-mentioned conditions by certifying that borohydride exchange resin can simultaneously carry out reduction of disulfide compounds and reduction of pertechnetate or perrhenate under the mild condition and that the labelling of technetium or rhenium with sulfide compounds with high radiochemical purity and high yield can be carried out.

SUMMARY OF THE INVENTION

A method for labelling a sulfide compound with technetium or rhenium, comprising the reaction of a disulfide compound with pertechnetate or perrhenate in the presence of borohydride exchange resin to obtain a complex of technetium or rhenium with the sulfide compound.

An object of the present invention is to provide a method for labelling technetium or rhenium with a sulfide compound.

Another object of the present invention is to provide a method for the preparation of technetium or rhenium complex with sulfide compounds by obtaining them from disulfide compounds as a starting material.

An object of the present invention is still to provide a method for the preparation of [$^{99m}Tc$] Tc—S or [$^{188}Re$] Re—S complex by reacting disulfide compounds with pertechnetate ($TcO_4^-$) or perrhenate ($ReO_4^-$) in the presence of borohydride exchange resin.

Further, an object of the present invention is to provide a kit for use in labelling technetium or rhenium, comprising a disulfide compound and a borohydride exchange resin.

BRIEF DESCRIPTION OF THE DRAWINGS

The above and other objects, features and other advantages of the present invention will be more clearly understood from the following detailed descriptions taken in conjunction with the accompanying drawings, in which.

DETAILED DESCRIPTION OF THE INVENTION

Figure 1A:
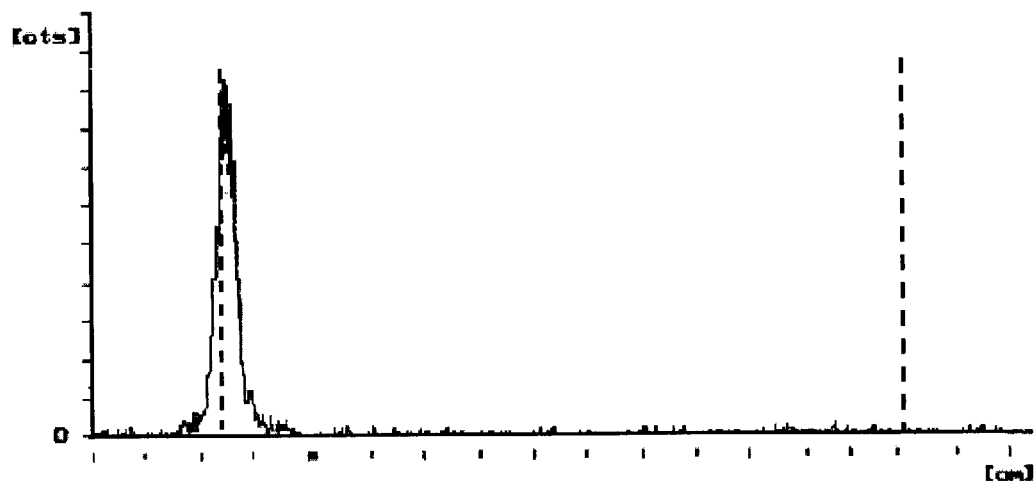
FIG. 1a shows the result of performing thin layer chromatography of a technium complex prepared in Example 1 by using acetone as a developing solvent.

The present invention provides a method for labelling technetium or rhenium with sulfide compounds, more particularly the method comprises the steps of reacting pertechnetate ($TcO_4^-$) or perrhenate ($ReO_4^-$) with disulfide compounds in the presence of borohydride exchange resin, whereby the borohydride exchange resin plays an essential role in reducing the S—S bond in disulfide compound to a sulfide compound and the pertechnetate or perrhenate to technetium or rhenium with low oxidation state simultaneously, and thereby obtaining directly from the disulfide compound a technetium or rhenium labelled sulfide compound, [$^{99m}Tc$] Tc—S or [$^{188}Re$] Re—S complex.

A "sulfide compound" in the present invention refers to a reduced form of a S—S bond in a disulfide compound.

A "disulfide compound" in the present invention refers to all disulfide compounds having a S—S bond. The disulfide compound is unsaturated or substituted with amine group, carboxyl group, isocyanate group, alcohol group, ester group, halogen atom group, alkoxyl group, sulfonate group, nitro group, amide group, nitrite group and isonitrile group, wherein they do not affect on the chelation. Examples of disulfide compounds useful in the present invention include diamine disulfide compound, dicarboxyl disulfide compound, heterocyclic diulfide compound and dialcohol disulfide compound. More particularly, a disulfide compounds can be trans-1,2-dithiane-4,5-diol, 6,6'-dithiodinicotinic acid, L-cysteine.HCl.H$_2$O, 3,3,10,10-tetramethyl-1,2-dithia-5,8-diazacyclodecane, DL-dimercaptosuccinic acid, or 1-thio-β-D-gloucose. When the functional group is substituted with amine or isocyanate in the molecule, the unpaired electrons of the substitute readily tends to be a coordination bond.

The method is described in more detail in the following:

First, a disulfide compound is converted into a sulfide compound when a S—S bond is broken in the presence of borohydride exchange resin. Technetium ($^{99m}Tc$) or rhenium ($^{188}Re$) reduced in the form of pertechnetate or perrhenate in the presence of borohydride exchange resin is provided to low oxidation state. The reduced technetium or rhenium spontaneously reacts with reduced sulfide compound, and thus forming a [$^{99m}Tc$] Tc—S or a [$^{188}Re$] Re—S complex.

The reaction should be carried out in situ condition under an inert atmosphere, i.e., under a nitrogen atmosphere.

The method of the present invention is not particularly limited to the procedure of adding pertechnetate or perrhenate, that is, the complex of technetium or rhenium with sulfide formed by adding pertechnetate or perrhenate into the mixture of the disulfide compounds and borohydride exchange resin, and by adding the disulfide compounds first and then pertechnetate or perrhenate successively into borohydride exchange resin. In particular, the mixture of the disulfide compounds and borohydride exchange resin is lyophilized.

As shown in the reaction, the borohydride exchange resin plays an essential role in reducing the S—S bond in disulfide compound to a sulfide compound and the pertechnetate or perrhenate to technetium or rhenium with low oxidation state simultaneously, and thereby obtaining directly from the disulfide compound a technetium or rhenium labelled sulfide compound, [$^{99m}Tc$] Tc—S or [$^{188}Re$] Re—S complex.

A borohydride exchange resin comprises a borohydride ion ($BH_4^-$) bind to a cation, which is supported on a polymer, and the cation used for adhering the borohydride ion has quaternary ammonium functionality. The borohydride exchange resin is usually used in the amount enough to reduce both a disulfide compound and pertechnetate or perrhenate.

Figure 10:
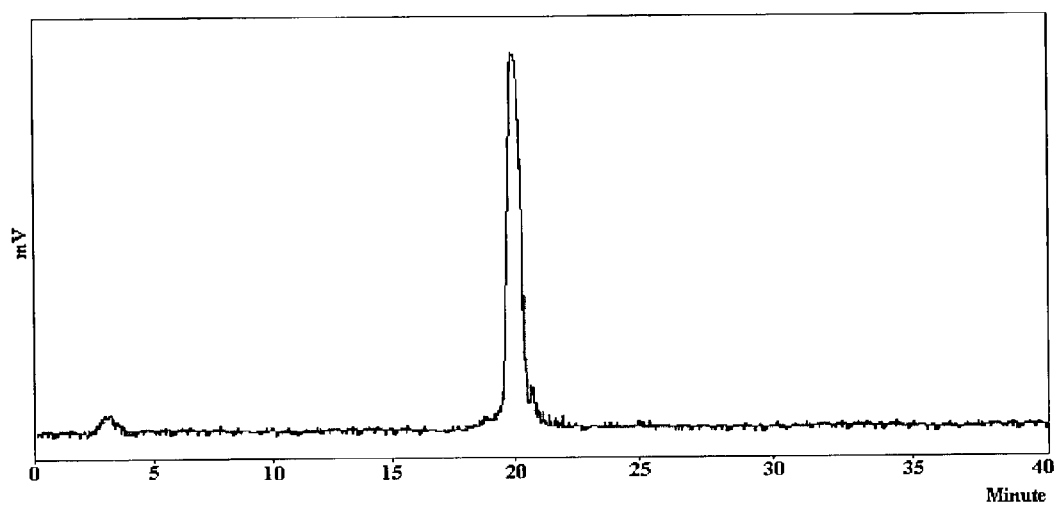
FIG. 10 shows the result of HPLC analysis of a rhenium complex prepared in Example 5.

The chelation is accomplished in a suitable medium at room temperature depending on the chemical reagents used. The targeted labelled complex can be obtained by simply filtering the reactant using the membrane filter having a pore size of 0.2 μm with high radiochemical purity and high yield. Additionally, if the synthesized labelled complex is an aseptic radiophamaceuticals, it can be applied to clinic practices immediately. Generally, the reaction is completed within 10 to 30 minutes depending on the ligands and conditions used. Based on the preferred embodiment of the present invention, we recognized that the technetium or rhenium labelled complex prepared by the method of the present invention had 99% of radiochemical purity and more than 95% of labelling yield (FIG. 1 or FIG. 10).

The present invention provides a kit for labelling technetium or rhenium. Wherein the said kit comprises a disulfide compound and a borohydride exchange resin. In clinical, the kit is applied to a patient right after the in situ labelling process by adding pertechnetate and perrhenate to a vessel including the disulfide compound and the borohydride exchange resin. In order to secure the storage stability, the kit should be preferably lyophilized or dried at room temperature. If the lyophilization of the kit is impossible, the kit should be stored frozen. It is more preferable for keeping in sterilized and sealed condition containing no pyrogenic materials, and it is also preferable for the reaction vessel to be purged with inert gas such as nitrogen gas, thereby being maintained under a nitrogen gas atmosphere. In order to secure the storage stability, the kit of the present invention may include a commonly used annex such as sodium citrate and manitol which are well known to anyone skilled in the present art.

The method and kit for use in labelling technetium and rhenium in the present invention can directly obtain a technetium or rhenium labelled sulfide complex, [$^{99m}Tc$] Tc—S or [$^{188}Re$] Re—S complex, from the disulfide compounds in the presence of borohydride exchange resin, which simultaneously reduces the disulfide compound and the pertechnetate or perrhenate so that the reduced forms readily coordinate to complex.

The method and kit for use in labelling technetium and rhenium in the present invention can skip the synthetic step of thiol-protected S-precursor and particularly as for technetium, no other reducing agents are necessary.

Therefore, the kit for use in labelling technetium or rhenium prepared in the method of the present invention is simple and efficient and thus, the kit is useful for high value-added radiophamaceuticals.

The present invention is explained more specifically in the following examples. The primary objective of these examples is to explain the present invention more particularly, and the scopes of the present invention are not to be limited by these examples. Anyone skilled in the present art can modify or improve the present specification within the range that the scopes and the objectives of the present invention are not changed.

EXAMPLE 1

An aqueous solution wherein 2 mg of trans-1,2-dithiane-4,5-diol was dissolved in 0.1 ml of distilled water and 0.1 mg of an aqueous solution of sodium pertechnetate [$^{99m}TcO_4^-$] (5 mCi) were injected simultaneously into a vial containing 3 mg of borohydride exchange resin under a nitrogen atmosphere. After the injected reactants are homogenously mixed, they were further stirred for 30 minutes at room temperature. Thus, technetium labelled sulfide complex, [$^{99m}Tc-S$], was obtained by filtration using the membrane filter having a pore size of 0.2 μm.

EXAMPLE 2

A labelling technetium labelled sulfide complex, [$^{99m}Tc-S$], was prepared in the same manner under the same conditions as in Example 1, except that the said technetium complex was prepared by injecting an aqueous solution wherein 1 mg of 6,6'-dithiodinicotinic acid was dissolved in 0.1 ml of distilled water and an aqueous solution of sodium pertechnetate, [Na$^+$] [$^{99m}TcO_4^-$] (5mCi), simultaneously into a vial containing 5 mg of borohydride exchange resin, after dissolving 10 mg of 6,6'-dithiodinicotinic acid in 0.5 N sodium hydroxide solution till adjusted to pH 9.

EXAMPLE 3

A labelling technetium labelled sulfide complex, [$^{99m}Tc-S$], was prepared in the same manner under the same conditions as in Example 1, except that the said technetium complex was prepared by injecting an aqueous solution wherein 1 mg of L-cysteine.HCl.H$_2$O was dissolved in 0.1 ml of distilled water and 0.1 ml of aqueous solution of sodium pertechnetate, [Na$^+$] [$^{99m}TcO_4^-$] (5mCi), simultaneously into a vial containing 5 mg of borohydride exchange resin.

EXAMPLE 4

A labelling technetium labelled sulfide complex, [$^{99m}Tc-S$], was prepared in the same manner under the same conditions as in Example 1, except that the said technetium complex was prepared by injecting an aqueous solution wherein 1 mg of 3,3,10,10-tetramethyl-1,2-dithia-5,8-diazacyclodecane was dissolved in 0.1 ml of distilled water and 0.1 ml of aqueous solution of sodium pertechnetate, [Na$^+$] [$^{99m}TcO_4^-$] (5mCi), simultaneously into a vial containing 5 mg of borohydride exchange resin.

EXAMPLE 5

An aqueous solution wherein 1 mg of 3,3,10,10-tetramethyl-1,2-dithia-5,8-diazacyclodecane was dissolved in 0.1 ml of distilled water, an aqueous solution wherein 0.5 mg of stannous chloride dihydrate was dissolved in 0.1 ml of 0.005 N HCl, and 0.1 ml of aqueous solution of sodium perrhenate, [Na$^+$] [$^{99m}ReO_4^-$] (5 mCi) were injected simultaneously into a vial containing 5 mg of borohydride exchange resin. After the injected reactants were mixed well, they were reacted in boiling water for 15 minutes, and then cooled at room temperature. After stirring, a labelling rhenium labelled sulfide complex, [$^{188}Re-S$], was obtained by filtering using the membrane filter having a pore size of 0.2 μm.

COMPARATIVE EXAMPLE 1

A labelling rhenium-sulfide complex was prepared in the same manner under the same conditions as in Example 1, except that an aqueous solution wherein 1 mg of 3,3,10,10-tetramethyl-1,2-dithia-5,8-diazacyclodecane was dissolved in 0.1 ml of distilled water, 0.1 ml of sodium pertechnetate [$^{99m}TcO_4^-$] (5 mCi) solution, and a solution wherein 0.5 mg of stannous chloride dihydrate was dissolved in 0.1 ml of 0.005 N HCl were injected simultaneously into a vial containing 5 mg of borohydride exchange resin under a nitrogen atmosphere.

EXPERIMENTAL EXAMPLE 1

Figure 1B:
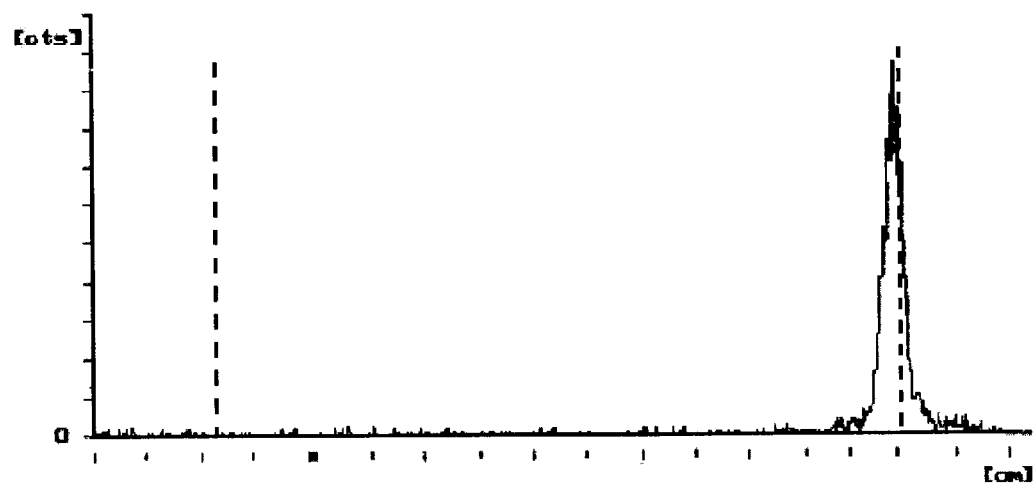
FIG. 1b shows the result of performing thin layer chromatography of a technium complex prepared in Example 1 by using methanol: hydrochloric acid (99.5:0.5) as a developing solvent.

The radiochemical purity of the technetium labelled sulfide complex prepared in Example 1 was measured using thin layer chromatography. FIG. 1a shows the result along with acetone as an eluting solvent, and FIG. 1b shows the result along with methanol: hydrochloric acid (99.5:0.5) as an eluting solvent. Based on FIG. 1a and FIG. 1b, the radiochemical purity of the technetium labelled sulfide, which starts from a disulfide compound, trans-1,2-dithiane-4,5-diol, prepared in Example 1 was more than 99%.

EXPERIMENTAL EXAMPLE 2

The technetium-sulfide complex prepared in Example 1 was measured by high performance liquid chromatography (HPLC) for the labelling yield. The result was shown in FIG. 2. The condition was as follows; a mobile phase was used on a water/acetonitrile and the flow rate was 1 ml/min.

Figure 2:
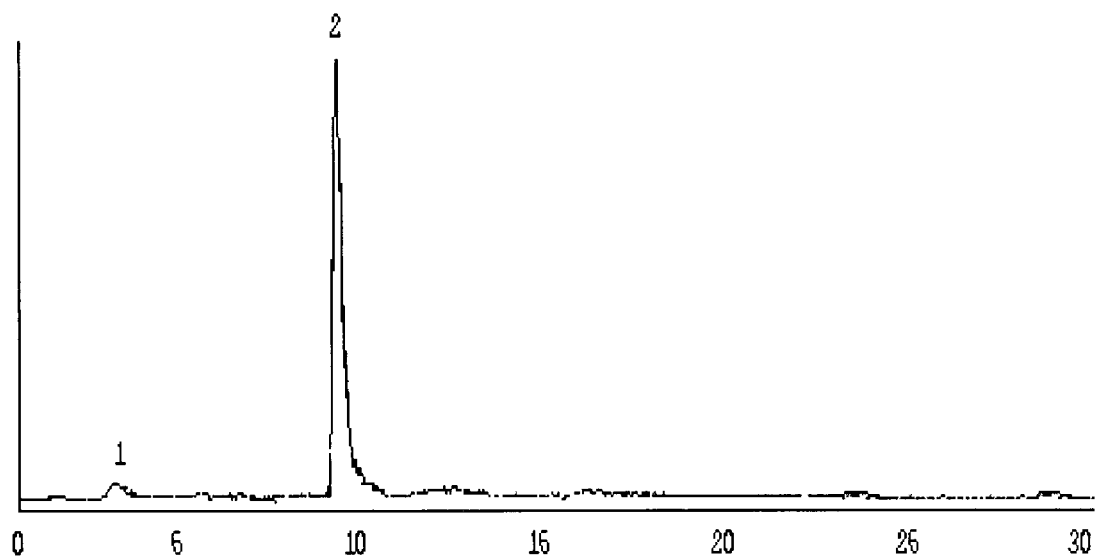
FIG. 2 shows the result of HPLC (high performance liquid chromatograph) analysis of a technetium complex prepared in Example 1.

As shown in FIG. 2, two peaks were observed. One peak was observed at 3 min of the retention time corresponding to $^{99m}TcO_4^-$, and another peak at 10 min thereafter, which was the purposed technetium-sulfide complex, and thus having labelling yield of more than 98%.

EXPERIMENTAL EXAMPLE 3

The radiochemical purity of the labelling technetium-sulfide complex prepared in Example 2 was measured in the same manner under the same solvent conditions as in Experimental Example 1. The result was shown in FIG. 3a and FIG. 3b.

Figure 3A:
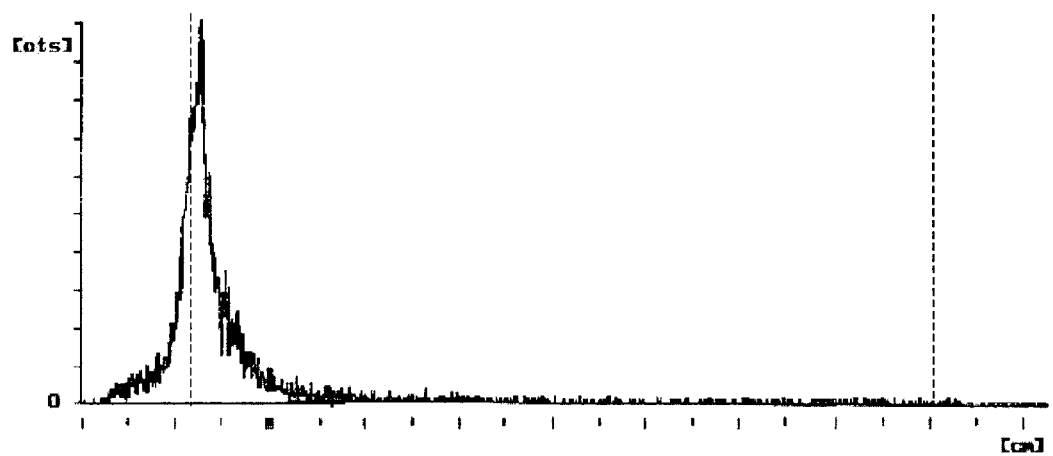
FIG. 3a shows the result of performing thin layer chromatography of a technium complex prepared in Example 2, by using acetone as a developing solvent.
Figure 3B:
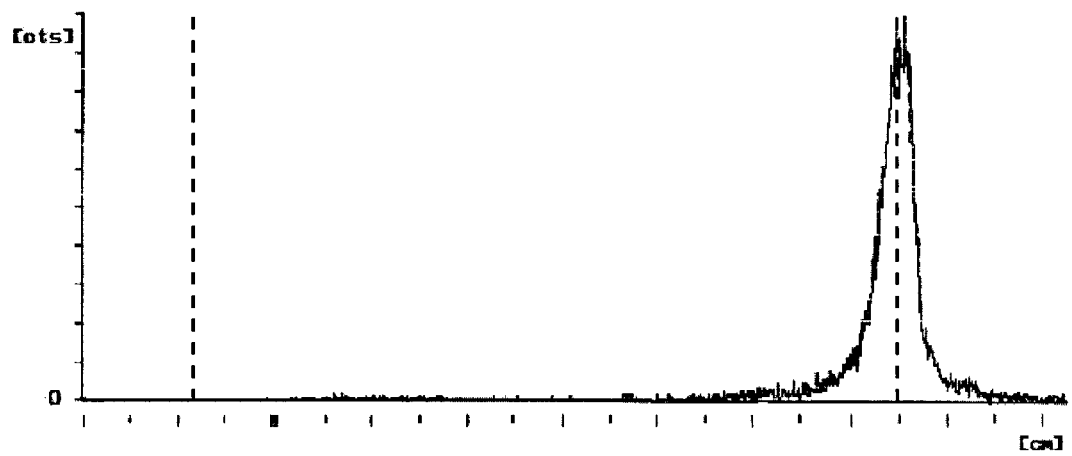
FIG. 3b shows the result of performing thin layer chromatography of a technium complex prepared in Example 2 by using methanol: hydrochloric acid (99.5:0.5) as a developing solvent.

Based on FIG. 3a and FIG. 3b, the radiochemical purity of the technetium labelled sulfide, which starts from the disulfide compound, 6,6'-dithiodinicotinic acid, prepared in Example 2 was more than 99%.

EXPERIMENTAL EXAMPLE 4

The technetium-sulfide complex prepared in Example 2 was conducted by HPLC in the same conditions as in Experimental Example 2. The result was shown in FIG. 4.

Figure 4:
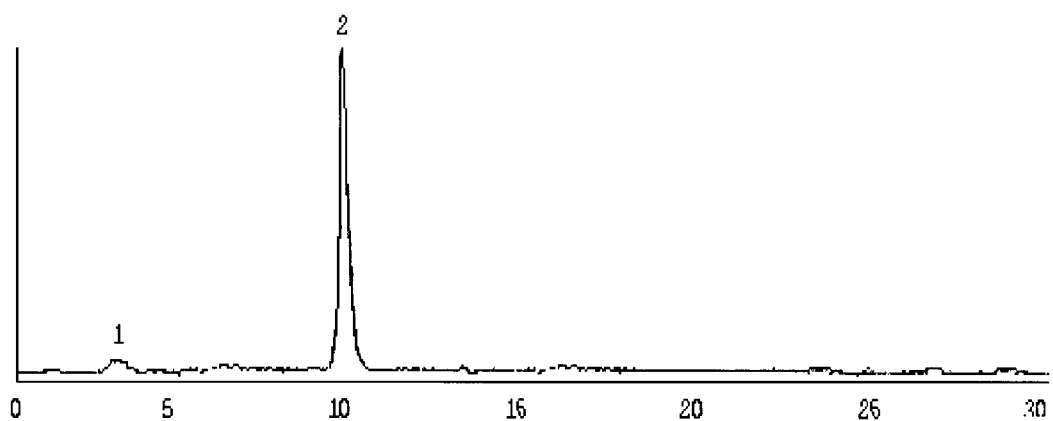
FIG. 4 shows the result of HPLC analysis of a technetium complex prepared in Example 2.

From FIG. 4, one peak was observed within 3 min of the retention time corresponding to $^{99m}TcO_4^-$ and another peak appeared at 10.1 min of the retention time, which was the purposed technetium-sulfide complex prepared in Example 2, having labelling yield of more than 98%.

EXPERIMENTAL EXAMPLE 5

The radiochemical purity of the technetium labelled sulfide complex prepared in Example 3 was measured in the same manner using thin layer chromatography in Experimental Example 1 except that the eluting solvent was saline.

Figure 5A:
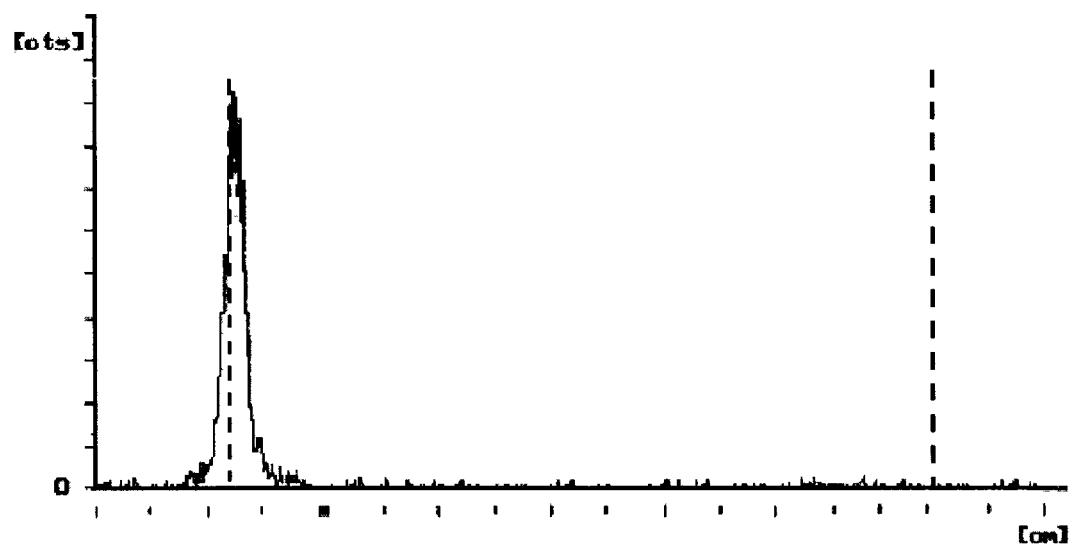
FIG. 5a shows the result of performing thin layer chromatography of a technium complex prepared in Example 3 by using acetone as a developing solvent.
Figure 5B:
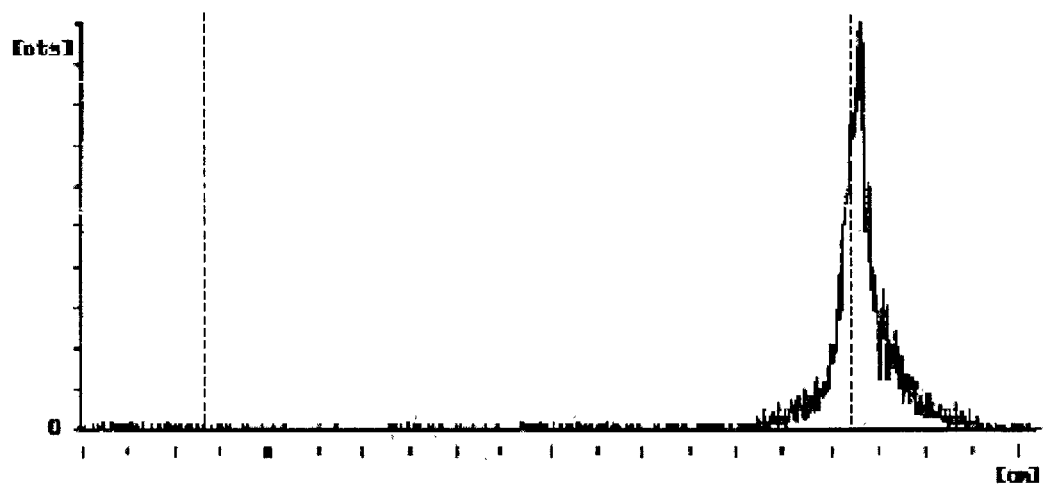
FIG. 5b shows the result of performing thin layer chromatograph of a technetium complex prepared in Example 3 by using saline as a developing solvent.

Based on the results of FIG. 5a and FIG. 5b, the radiochemical purity of the technetium labelled sulfide, which starts from the disulfide compound, L-cysteine.HCl.H$_2$O, prepared in Example 3 was more than 99%.

EXPERIMENTAL EXAMPLE 6

The technetium-sulfide complex prepared in Example 3 was measured by HPLC for the labelling yield. The result was shown in FIG. 6. The condition was as follows; a mobile phase was used on pH 5 of triethylammonium phosphate buffer solution and methanol, and the flow rate was 1 ml/min.

Figure 6:
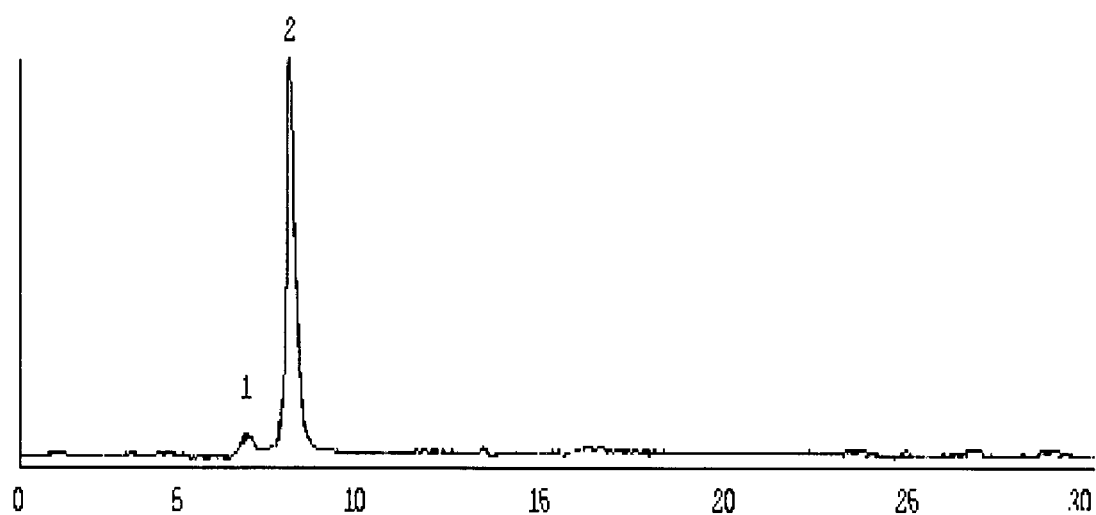
FIG. 6 shows the result of HPLC analysis of a technetium complex prepared in Example 3.

As shown in FIG. 6, two peaks were observed. One peak was observed at 7.2 min of the retention time corresponding to $^{99m}TcO_4^-$, another peak appeared at 10 min thereafter, which was the purposed technetium-sulfide complex, and thus having labelling yield of more than 95%.

EXPERIMENTAL EXAMPLE 7

Figure 7A:
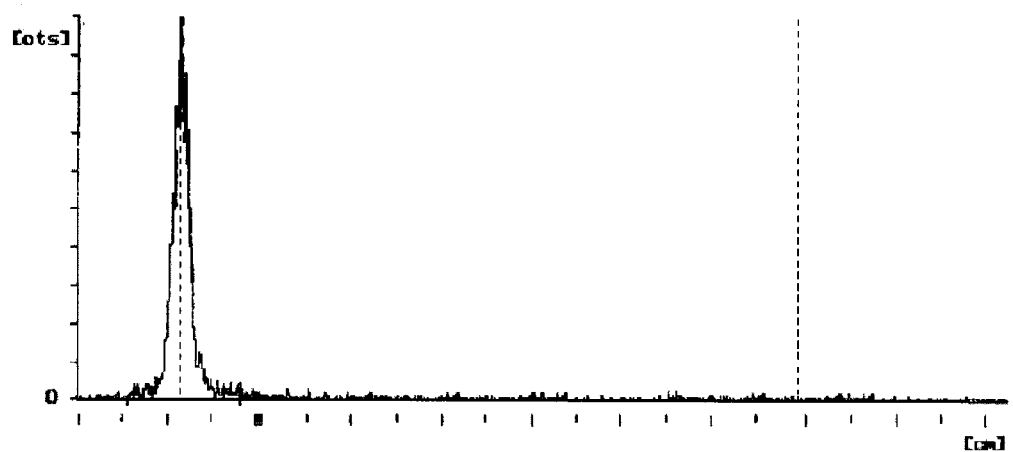
FIG. 7a shows the result of performing thin layer chromatography of a technium complex prepared in Example 4 by using acetone as a developing solvent.
Figure 7B:
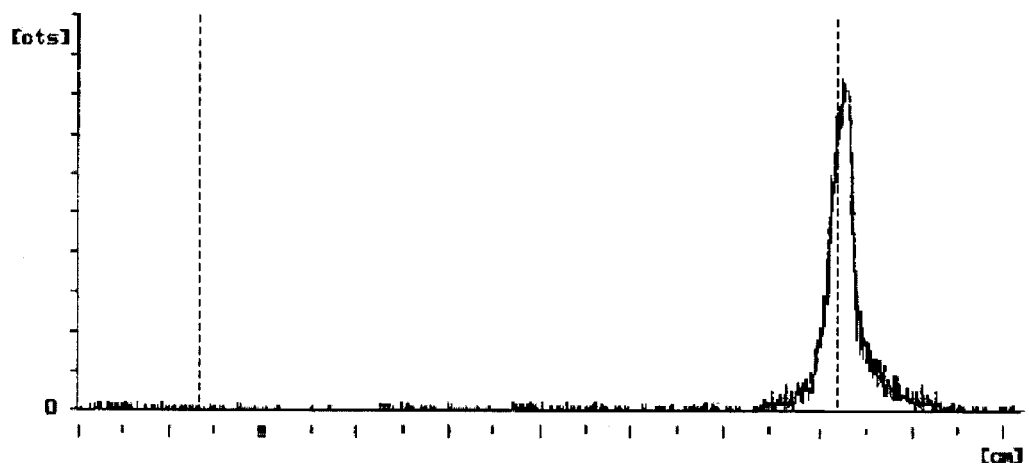
FIG. 7b shows the result of performing thin layer chromatography of a technium methanol: hydrochloric acid (99.5:0.5) prepared in Example 4 as a developing solvent.

The radiochemical purity of the technetium labelled sulfide complex prepared in Example 4 was measured in the same manner under the same solvent conditions as in Experimental Example 1. The results were shown in FIG. 7a and FIG. 7b, which the radiochemical purity of the labelling technetium-sulfide, which starts from the disulfide compound, 3,3,10,10-tetramethyl-1,2-dithia-5,8-diazacyclodecane, prepared in Example 4 was more than 99%.

EXPERIMENTAL EXAMPLE 8

The technetium-sulfide complex prepared in Example 4 was conducted by HPLC in the same conditions as in Experimental Example 2. The result was shown in FIG. 8.

Figure 8:
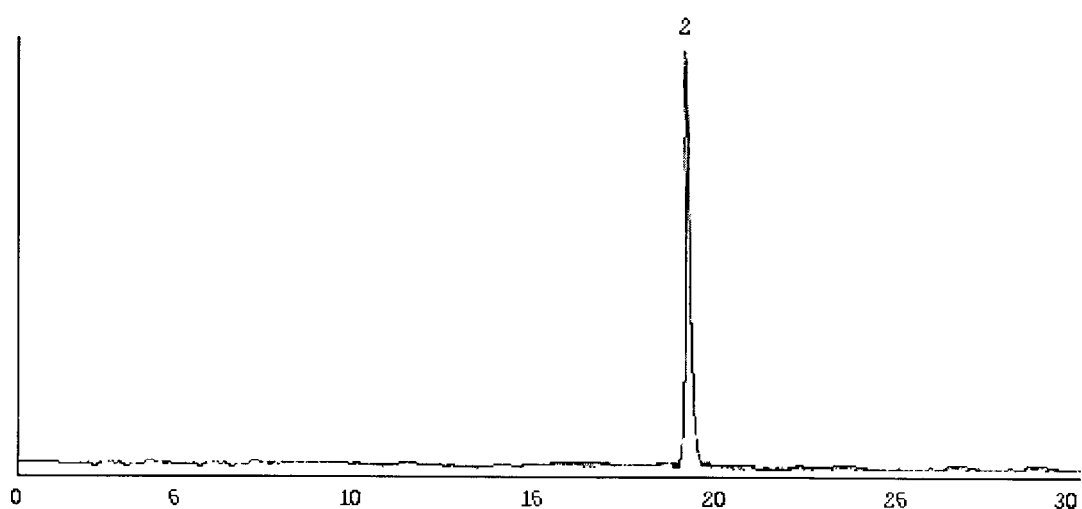
FIG. 8 shows the result of HPLC analysis of a technetium complex prepared in Example 4.

As shown in FIG. 8, one peak was observed within 3 min of the retention time corresponding to $^{99m}TcO_4^-$ and another peak appeared at 19.4 min of the retention time, which was the purposed technetium-sulfide complex prepared in Example 4, having labelling yield of more than 98%.

EXPERIMENTAL EXAMPLE 9

Figure 9:
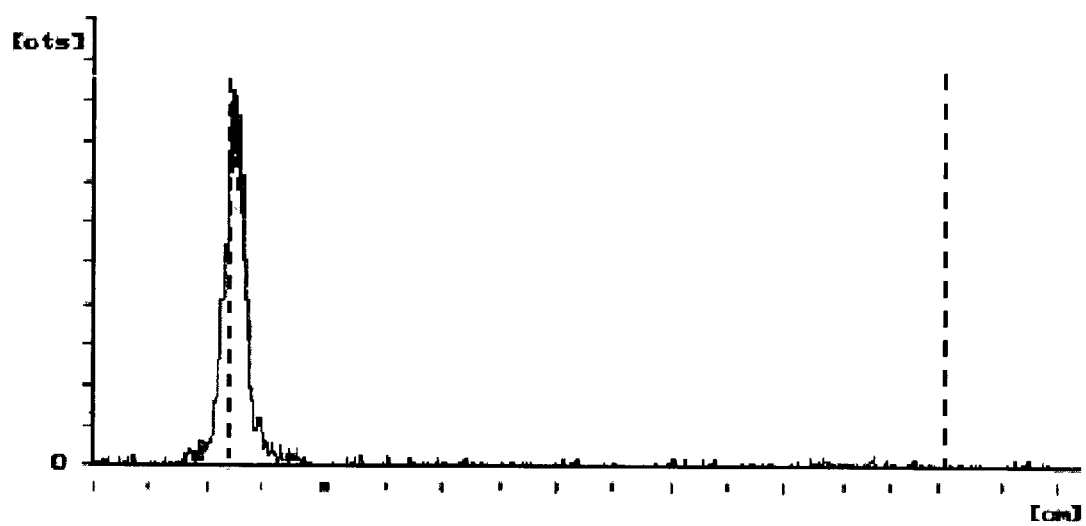
FIG. 9 shows the result of performing thin layer chromatography a rhenium complex prepared in Example 5 by using acetone as a developing solvent.

The radiochemical purity of the rhenium labelled sulfide complex prepared in Example 5 was measured in the same manner under the same solvent conditions as in Experimental Example 1. The result was shown in FIG. 9, which showed high radiochemical purity of the rhenium labelled sulfide.

EXPERIMENTAL EXAMPLE 10

The rhenium-sulfide complex prepared in Example 5 was conducted by HPLC in the same conditions as in Experimental Example 2. The result was shown in FIG. 10.

As shown in FIG. 10, it one peak was observed within 2.8 min of the retention time corresponding to $^{188}ReO_4^-$ and another peak appeared at 20.1 min of the retention time, which was the purposed rhenium-sulfide complex prepared in Example 5, having labelling yield of more than 98%.

From the results, all of the technetium or rhenium labelled complexes prepared by the method of the present invention were confirmed to have a radiochemical purity of 99% and more and a labelling yield of 95% and more. Meanwhile, technetium or rhenium labelled complex was not observed in Comparative Example 1 using stannous chloride.dihydrate instead of borohydride exchange resin as a reducing agent.

Therefore, the method and kit in the present invention can directly label disulfide compounds with technetium or rhenium by simultaneously reducing the disulfide compound and the petechnetate or perrhenate using borohydride exchange resin.

In addition, the method of the present invention can skip the synthetic step of thiol-protected S-precursor and particularly as for technetium, no other reducing agents are necessary. The kit prepared in the present invention is useful for high value-added radiopharmaceuticals.

What is claimed is:

1. A method for labelling a sulfide compound with technetium or rhenium, comprising the reaction of a disulfide compound with pertechnetate or perrhenate in the presence of borohydride exchange resin to obtain a complex of technetium or rhenium with the sulfide compound.

2. The method according to claim 1, wherein the complex of technetium or rhenium with sulfide is formed by adding pertechnetate or perrhenate into the mixture of the disulfide compound and borohydride exchange resin.

3. The method according to claim 2, wherein the mixture of the disulfide compound and borohydride exchange resin is lyophilized.

4. The method according to claim 1, wherein said disulfide compound is unsaturated or substituted with amine group, carboxyl group, isocyanate group, alcohol group, ester group, halogen atom group, alkoxyl group, sulfonate group, nitro group, amide group, nitrile group or isonitrile group.

5. The method according to claim 1, wherein said disulfide compound is diamine disulfide compound, dicarboxyl disulfide compound, heterocyclic diulfide compound or dialcohol disulfide compound.

6. The method according to claim 1, wherein said disulfide compound is trans-1,2-dithiane-4,5-diol, 6,6'-dithiodinicotinic acid, L-cysteine.HCl.H$_2$O, 3,3,10,10-tetramethyl-1, 2-dithia-5,8-diazacyclodecane, DL-dimercaptosuccinic acid, or 1-thio-β-D-gloucose.

7. The method according to claim 1, wherein the complex of technetium or rhenium with sulfide is formed by adding the disulfide compound first and then pertechnetate or perrhenate successively into borohydride exchange resin.

8. A kit for use in labeling technetium or rhenium, comprising a disulfide compound and borohydride exchange resin.

9. The kit according to claim 8, wherein said kit is kept in sterilized and sealed condition maintained under a nitrogen gas atmosphere.

* * * * *

UNITED STATES PATENT AND TRADEMARK OFFICE
CERTIFICATE OF CORRECTION

PATENT NO. : 6,979,431 B2
DATED : December 27, 2005
INVENTOR(S) : Kyung Bae Park et al.

It is certified that error appears in the above-identified patent and that said Letters Patent is hereby corrected as shown below:

<u>Column 8,</u>
Line 39, change "diulfide" to -- disulfide --.

Signed and Sealed this

Seventh Day of March, 2006

JON W. DUDAS
*Director of the United States Patent and Trademark Office*